United States Patent
Krimsky

(10) Patent No.: US 10,973,396 B2
(45) Date of Patent: Apr. 13, 2021

(54) ENHANCED ABLATION AND VISUALIZATION TECHNIQUES

(71) Applicant: COVIDIEN LP, Mansfield, MA (US)

(72) Inventor: William S. Krimsky, Forest Hill, MD (US)

(73) Assignee: COVIDIEN LP, Mansfield, MA (US)

(*) Notice: Subject to any disclaimer, the term of this patent is extended or adjusted under 35 U.S.C. 154(b) by 108 days.

(21) Appl. No.: 15/865,431

(22) Filed: Jan. 9, 2018

(65) Prior Publication Data
US 2018/0214012 A1 Aug. 2, 2018

Related U.S. Application Data

(60) Provisional application No. 62/451,832, filed on Jan. 30, 2017, provisional application No. 62/451,836, filed on Jan. 30, 2017.

(51) Int. Cl.
*A61B 1/012* (2006.01)
*A61B 1/00* (2006.01)
(Continued)

(52) U.S. Cl.
CPC .......... *A61B 1/012* (2013.01); *A61B 1/00087* (2013.01); *A61B 1/015* (2013.01); *A61B 1/018* (2013.01); *A61B 1/2676* (2013.01); *A61B 5/0036* (2018.08); *A61B 5/01* (2013.01); *A61B 8/12* (2013.01); *A61B 10/0233* (2013.01); *A61B 5/0538* (2013.01); *A61B 5/061* (2013.01); *A61B 5/4836* (2013.01); *A61B 5/7445* (2013.01); *A61B 6/032* (2013.01); *A61B 10/04* (2013.01); *A61B 18/1492* (2013.01);
(Continued)

(58) Field of Classification Search
CPC ......... A61B 1/012; A61B 1/018; A61B 1/015; A61B 2018/00541; A61B 10/04
See application file for complete search history.

(56) References Cited

U.S. PATENT DOCUMENTS

| 6,188,355 B1 | 2/2001 | Gilboa |
| 6,475,216 B2 | 11/2002 | Mulier et al. |

(Continued)

FOREIGN PATENT DOCUMENTS

| WO | 00/10456 A1 | 3/2000 |
| WO | 01/67035 A1 | 9/2001 |
| WO | 2010004570 A1 | 1/2010 |

OTHER PUBLICATIONS

Extended European Search Report dated Jun. 18, 2018 and issued in corresponding European Patent Application No. 18153816.
(Continued)

*Primary Examiner* — Lauren P Farrar

(57) ABSTRACT

A system and method for enhancing diagnosis and treatment including an extended working channel defining an elongated passageway and adapted to extend through the bronchoscope and into a luminal network, an opening operably associated with the extended working channel and in fluid communication with the luminal network, and a medical instrument configured for insertion through the extended working channel, wherein during operation, apposition of tissue on the extended working channel or medical instrument isolates at least a portion of a luminal network in which the extended working channel is inserted.

19 Claims, 5 Drawing Sheets

(51) Int. Cl.

| | | |
|---|---|---|
| *A61B 1/018* | (2006.01) | |
| *A61B 1/015* | (2006.01) | |
| *A61B 5/00* | (2006.01) | |
| *A61B 1/267* | (2006.01) | |
| *A61B 5/01* | (2006.01) | |
| *A61B 8/12* | (2006.01) | |
| *A61B 10/02* | (2006.01) | |
| *A61B 90/00* | (2016.01) | |
| *A61B 18/18* | (2006.01) | |
| *A61B 10/04* | (2006.01) | |
| *A61B 17/00* | (2006.01) | |
| *A61B 34/10* | (2016.01) | |
| *A61B 34/20* | (2016.01) | |
| *A61B 5/053* | (2006.01) | |
| *A61B 5/06* | (2006.01) | |
| *A61B 6/03* | (2006.01) | |
| *A61B 18/14* | (2006.01) | |
| *A61B 18/00* | (2006.01) | |
| *A61B 5/0538* | (2021.01) | |

(52) U.S. Cl.
CPC ..... *A61B 18/1815* (2013.01); *A61B 2010/045* (2013.01); *A61B 2017/00561* (2013.01); *A61B 2017/00566* (2013.01); *A61B 2017/00809* (2013.01); *A61B 2018/00541* (2013.01); *A61B 2018/00577* (2013.01); *A61B 2018/1861* (2013.01); *A61B 2034/105* (2016.02); *A61B 2034/2051* (2016.02); *A61B 2090/0811* (2016.02); *A61B 2090/397* (2016.02)

(56) References Cited

U.S. PATENT DOCUMENTS

| | | | |
|---|---|---|---|
| 6,770,070 B1* | 8/2004 | Balbierz | A61B 10/04 600/566 |
| 2003/0216730 A1* | 11/2003 | Barry | A61B 18/1482 606/45 |
| 2003/0233099 A1 | 12/2003 | Danaek et al. | |
| 2005/0027165 A1* | 2/2005 | Rovegno | A61B 1/012 600/154 |
| 2012/0149978 A1* | 6/2012 | Olivera | A61B 5/1076 600/104 |
| 2014/0046174 A1 | 2/2014 | Ladtkow et al. | |
| 2014/0046315 A1 | 2/2014 | Ladtkow et al. | |
| 2014/0088457 A1* | 3/2014 | Johnson | A61B 17/12104 600/567 |
| 2014/0270441 A1 | 9/2014 | Baker | |
| 2014/0276033 A1 | 9/2014 | Brannan et al. | |
| 2014/0281961 A1 | 9/2014 | Baker | |
| 2014/0282216 A1 | 9/2014 | Baker | |
| 2015/0073211 A1 | 3/2015 | Dickhans et al. | |
| 2015/0141809 A1 | 5/2015 | Costello et al. | |
| 2015/0141869 A1 | 5/2015 | Costello et al. | |
| 2015/0265257 A1* | 9/2015 | Costello | A61B 1/2676 600/424 |
| 2016/0051327 A1 | 2/2016 | Brannan | |
| 2016/0184013 A1 | 6/2016 | Brannan et al. | |
| 2017/0202543 A1 | 7/2017 | Herdina et al. | |
| 2017/0245740 A1 | 8/2017 | Krimsky et al. | |

OTHER PUBLICATIONS

International Search Report dated May 4, 2018 in corresponding International Application No. PCT/US2018/015155.
European Examination Report issued in corresponding Appl. No. EP 18153816.6 dated Jun. 11, 2019 (5 pages).

* cited by examiner

ENHANCED ABLATION AND VISUALIZATION TECHNIQUES

CROSS REFERENCE TO RELATED APPLICATION

The present application claims the benefit of and priority to U.S. Provisional Application Ser. No. 62/451,832, filed on Jan. 30, 2017, and U.S. Provisional Application Ser. No. 62/451,836, filed on Jan. 30, 2017. This application is related to U.S. patent application Ser. No. 15/865,560, filed on Jan. 9, 2018. The entire contents of each of the above applications are hereby incorporated herein by reference.

TECHNICAL FIELD

The present disclosure relates to surgical systems, and more particularly, to systems and methods of ablation techniques.

BACKGROUND

A large number of people suffer from lung disease, such as emphysema, chronic obstructive pulmonary disease ("COPD"), asthma, or cancer. Diseases such as emphysema result in poor airflow due to a breakdown of lung tissues. In patients suffering from emphysema the alveoli are no longer elastic and can become enlarged due to walls between the alveoli breaking down. As a result, the alveoli lose their shape and become floppy. This damage from emphysema leads to fewer and larger air sacs instead of many tiny ones. These large alveoli may be called bullae. One result of this breakdown of the alveoli is that the volume of gas exchange that can occur is reduced as the surface area of these fewer enlarged alveoli is less than the many smaller alveoli. Additionally, the weakened floppy alveoli easily expand during an inhalation. Because of the weakened condition, the air having entered the weakened alveoli cannot be forced out of the lungs during exhalation. Deoxygenated air is trapped inside of the damaged floppy alveoli. Additionally, lung diseases may result in build up or increased deposition of connective tissue within the lungs. Such build up or increased deposition of connective tissue increases density of lung tissue making it more difficult to penetrate.

Sometimes lesions form within the damaged floppy alveoli. The lesions that form within the alveoli also comprise the trapped air inside of the damaged floppy alveoli. Therefore, any medical instrument that is inserted into the lesion is then surrounded by air that is within the lesions. Additionally, lesions may also form within areas of increased connective tissue or scarring as well, resulting in increasing the amount of force necessary to insert a medical instrument through the tissue and into the lesion. Furthermore, since tissue does not divide along a straight line, inserting a medical instrument into tissue or penetrating a medical instrument through tissue often results in air-gaps being created between the tissue and the instrument itself. Further, the mere act of inserting an instrument into a target area must, necessarily, divide the tissue resulting in space for air to collect the instruments.

In procedures that involve using medical instruments that deliver energy, such as microwave energy, or other forms of therapies, such as chemotherapy, to attack a lesion, the air that surrounds the medical instrument creates numerous problems including inefficient delivery of energy or drug to attack the lesions. Further this air creates passageways for leakage of therapeutic substance away from the intended site. Additionally, the air from the lesions also affects medical devices that use ultrasound to generate images, resulting in poor or inaccurate images of the tissue of the lesion and surrounding the lesion. The present disclosure seeks to address at least some of the above-identified air related problems.

SUMMARY

According to an aspect of the present disclosure, apparatuses, methods and systems are provided that address the above mentioned needs. The present disclosure is directed in part to a system including an extended working channel defining an elongated passageway and adapted to extend through the bronchoscope and into a luminal network, an opening operably associated with the extended working channel and in fluid communication with the luminal network and medical instrument configured for insertion through the extended working channel. During operation, apposition of tissue in the direction of the extended working channel isolates at least a portion of a luminal network in which the extended working channel is inserted.

The opening may be connected to a vacuum source, such as a syringe. The vacuum source may generate a threshold amount of suction to remove air from at least a portion of a luminal network in which the extended working channel is inserted. A consistent zone may be formed around the medical instrument by suctioning the air from at least a portion of a luminal network in which the extended working channel is inserted using the opening operably associated with the extended working channel.

The opening may be connected to a liquid source, which provides for example saline. The system may include a valve in fluid communication with the liquid source and the opening such as a duckbill valve. A consistent zone may be formed around the medical instrument by injecting fluid from the fluid source through the opening in the extended working channel and into at least a portion of a luminal network in which the extended working channel is inserted.

The system may further include one or more balloons operably associated with the extended working channel to secure the extended working channel within the luminal network and isolate at least a portion of the luminal network. The opening may be located proximal of the distal end of the extended working channel.

A further aspect of the present disclosure is directed to a method including navigating an extended working channel through a bronchoscope to a target within a luminal network, inserting a medical instrument into the extended working channel; and apposing tissue on at least a portion of the extended working channel or medical instrument to isolate at least a portion of a luminal network in which the extended working channel is inserted.

Vacuum may be applied to the extended working channel to draw air from the luminal network to an opening formed in the extended working channel. The vacuum may draw air away from the distal end of the medical instrument. The method may include the generation of a consistent zone around the medical instrument.

A further aspect of the present disclosure is directed to a system including a medical instrument with a handle and an ablation probe, the ablation probe includes a microwave ablation antenna, a catheter attached to the medical instrument, an opening of the catheter is connected to an external source. During operation, apposition of a target tissue in a patient with the medical instrument isolates at least the portion of a target area in the patient including the target tissue.

In another aspect of the present disclosure, the handle of the medical instrument includes a housing unit and the catheter is configured to extend from the housing unit and retract into the housing unit.

In another aspect of the present disclosure, the catheter surrounds the ablation probe of the medical instrument.

In yet another aspect of the present disclosure, the external source is a vacuum source.

In yet another aspect of the present disclosure, the external source is a liquid source.

BRIEF DESCRIPTION OF THE DRAWINGS

Various aspects and features of the present disclosure are described herein below with references to the drawings, wherein.

DETAILED DESCRIPTION

Figure 1:
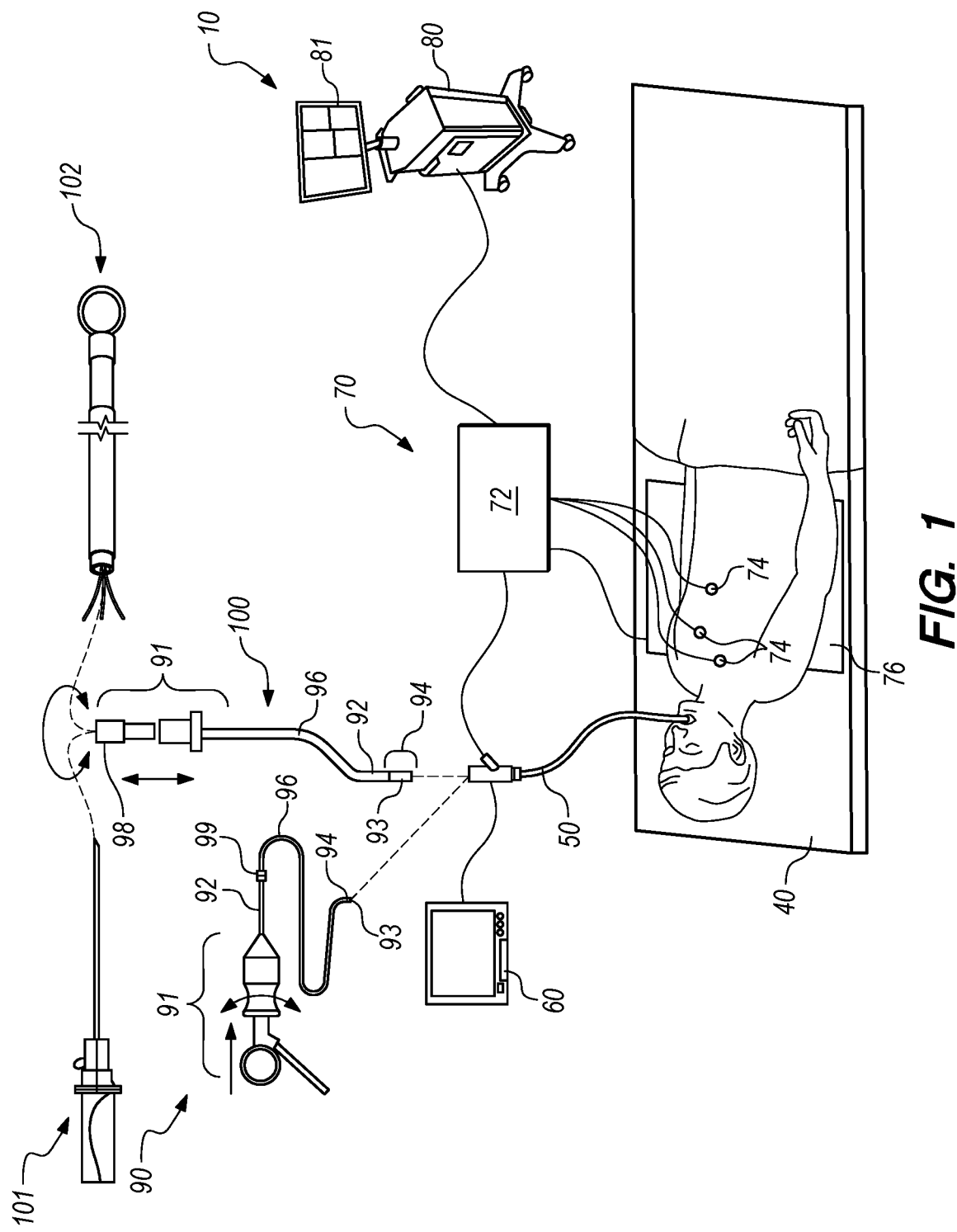
FIG. 1 is a perspective view of a system provided in accordance with the present disclosure configured for navigating a tool to a surgical site.

The present disclosure is directed to devices and systems for enhanced treatment options and effectiveness of surgical procedure. Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. Throughout this description, the term "consistent field" or "consistent zone" refers to an area in space within the body of a patient, where the permittivity of the area to microwave energy is less than the permittivity of air to microwave energy. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Lesions may form in various regions within the body. Some lesions may be accessible within an area of the body that is reachable using the airways of the patient. To approach or treat lesions that are within an area of the body of the patient that is reachable using the airways of the patient, a clinician may navigate a medical instrument, such as an ablation catheter; to the area affected by the lesion using airway based medical navigation procedures. But lesions may form in areas of the body that are difficult or impossible to reach by navigating only within the airways of the patient. To approach or treat lesions that are outside of the airways, a clinician may navigate a medical instrument, such as a biopsy or treatment catheter to the area affected by the lesion or the desired surgical site using off-airway surgical procedures involving puncturing a portion of the tissue of luminal network of the lungs (e.g. airways) and tunneling to the desired surgical site. This tunneling may be done either using a separate tunneling device, or in some instances using the medical instrument itself.

Lesions typically have different tissue density than tissue not affected by the disease. Each lesion may have a different tissue density from other lesions. For example, some lesions such as leipidic adenocarcinomas are partially solid. Lesions, as described herein, may be a nonspecific finding on a computed tomography (CT) scans typically described as ground-glass opacification or opacity. Further, scar tissue can give rise to new malignancies thus necessitating biopsy and treatment of this denser tissue. Still further, lesions may also be partially filled with air. Therefore, puncturing a lesion for treatment or performing a biopsy of the lesion may result in the medical instrument being surrounded by the air of the lesion potentially affecting the effectiveness.

When considering effective utilization of medical instruments, particularly treatment instruments such as microwave ablation or chemotherapy implements and visualization diagnostics such as ultrasound, it is important to note that a medical instrument that does not create apposition with the surrounding tissue will be less effective. As noted above, some of the targets themselves have air entrained within them as a consequence of the type of cancer (e.g., leipidic in situ adenoca), or location such as when diagnosing and treating a cavity lesion, such as infectious cavities. This effectiveness reduction is created by additional material interfaces between the medical instrument and the tissue to be treated. For example, when treating in the airways, air (a common insulator) adversely affects the efficiency of the energy transfer from the microwave radiator to the target. Additionally, the air in the lesions creates problems for ultrasound devices in producing images as ultrasound energy, like microwave energy, does not traverse air well. The result is an inefficient zone of treatment or inaccurate depiction of the tissue involved in the surgery, both of which may cause issues for clinicians in successfully treating the lesions.

The present disclosure provides apparatus, systems and techniques for creating a tissue-to-tool interface between the medical instrument and the lesion or the tissue affected by the lesion. The tissue-to-tool interface improves the efficiency of the zone of treatment, resulting in a more consistent field or consistent zone around the medical instrument. The improved field around the medical instrument allows for a more efficient delivery of energy or chemical therapies. Additionally, the improved field increases the accuracy and clarity of images of ultrasound devices, improving the visualization of the procedure for the clinicians.

In accordance with the present disclosure, one way to improve the consistent field or zone around the energy or treatment source is by the apposition of the target tissue to the medical instrument. With the apposition the target tissue against the medical instrument reduces the leakage of therapeutic substance away from the medical instrument or source or away from the target area can be minimized. Further, the energy transfer from modalities such as microwave, cryogenic, and RF ablation can be increased due to a reduction in resistance caused by the removal of air, which commonly acts as an insulator limiting efficient energy transfer. Still further, and for similar reasons apposition of the tissue against the medical instrument improves imaging clarity and accuracy.

In some embodiments, the tissue-to-tool interface between the medical instrument and the tissue may be created by suctioning air around the medical instrument such that the tissue is drawn closer to the medical instrument. The vacuum used in suctioning the air around medical instrument may be sufficient to draw the tissue closer to the medical instrument, however, may not be sufficient to induce atelectasis (i.e., the complete collapse of the tissue as a result of the withdrawal of the air in a given portion of the organ). In some embodiments, the tissue-to-tool interface between the medical instrument and the tissue may be created by injecting fluid that provides a more consistent environment or zone around medical instrument for delivering energy. Similarly, in other embodiments the apposition of the tissue to the therapy or treatment device can limit the ability of fluid or gas therapies or treatments from dispersing beyond the intended treatment site. Further, in some embodiments, images captured around the surgical site or the medical instrument may be projected on to one or more video monitors.

FIG. 1 depicts an electromagnetic navigation (EMN) system 10 is provided in accordance with the present disclosure. EMN system 10 may be employed in accordance with various example embodiments herein. An example of the EMN system is the ELECTROMAGNETIC NAVIGATION BRONCHOSCOPY® system currently sold by Medtronic, Inc. The specific number of components of the system 10 depicted in FIG. 1 and the arrangement and configuration thereof are provided for illustrative purposes only, and should be construed as limiting. EMN system 10 may be used to plan a pathway to target tissue, navigate a positioning assembly to the target tissue, navigate a biopsy tool to the target tissue to obtain a tissue sample from the target tissue and use the biopsy tool to digitally mark the location where the tissue sample was obtained, and place one or more echogenic markers at or around the target.

EMN system 10 includes an operating table 40 configured to support a patient, a bronchoscope 50 configured for insertion through the patient's mouth and/or nose into the patient's airways, monitoring equipment 60 coupled to bronchoscope 50 for displaying video images received from bronchoscope 50, a tracking system 70 including a tracking module 72, a plurality of reference sensors 74, an electromagnetic field generator 76, and a workstation 80 including software and/or hardware used to facilitate pathway planning, identification of target tissue, navigation to target tissue, and digitally marking the biopsy location.

Catheter guide assemblies may be used with EMN systems. FIG. 1 depicts two types of catheter guide assemblies 90, 100. Catheter guide assemblies 90, 100 are usable with the EMN system 10 and share a number of common components. Each of the catheter guide assemblies 90, 100 includes a handle 91, which is connected to an extended working channel (EWC) 96. The EWC 96 may be sized for placement into the working channel of a bronchoscope 50. In operation, a locatable guide (LG) 92, including an electromagnetic (EM) sensor 94, is inserted into the EWC 96 and locked into position such that the sensor 94 extends a desired distance beyond the distal tip of the EWC 96.

The location of the EM sensor 94, and thus the distal end of the EWC 96, within an electromagnetic field generated by the electromagnetic field generator 76 can be derived by the tracking module 72, and the workstation 80. Catheter guide assemblies 90, 100 have different operating mechanisms. In one embodiment, catheter guide assemblies 90, 100 contain a handle 91 that can be manipulated by rotation and compression to steer the distal tip 93 of the LG 92, extended working channel 96.

Valve 120 may be attached to EWC 96. In some embodiments, valve 120 may be used to suction air out of the patient's airways. A vacuum source (not shown) may be attached to valve 120 and may be used in suctioning air out of a certain area within the patient's airway. In some embodiments, valve 120 may permit injecting fluid, such saline, into a certain area within the patient. The area within the patient to which the fluid is injected may be based on the area where a medical instrument is to be used. In some embodiments, valve 120 may be attached perpendicularly to EWC 96. Additional details of valve 120 are described with respect to FIG. 2.

In some embodiments, one or more balloons (see e.g. FIG. 6) may extend from EWC 96. The balloons may extend laterally from EWC 96. A balloon may be located proximal to the distal end of the EWC 96. A balloon may also be located distally from the distal end of the EWC 96. The one or more balloons may be used to seal at least a portion of an airway. Upon sealing a portion of the airway, a medical instrument may be inserted in to EWC 96 and extended through the distal end of EWC 96 and to the target tissue.

In further embodiments, a port or opening may be located proximal to the distal end of EWC 96. The opening may be used to suction air from the space around the distal end of EWC 96 or to suction air surrounding a medical instrument. By suctioning a sufficient amount of air out from the distal end of EWC 96 or surrounding the medical instrument, the medical instrument is placed in apposition with the target or surgical site. Additional details of the opening or port proximal to the distal end of a EWC are described in FIG. 6.

For a more detailed description of the catheter guide assemblies 90, 100 and valves attached to extended working channels reference is made to commonly-owned U.S. Patent Application Publication No. 2014/0046315 filed on Mar. 15, 2013 by Ladtkow et al., and U.S. Provisional Patent Application No. 62/301,224 filed on Feb. 29, 2016 by Krimsky et al., the entire contents of each of which are hereby incorporated by reference.

As illustrated in FIG. 1, the patient is shown lying on an operating table 40 with a bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). The LG 92 and EWC 96 are selectively lockable relative to one another via a locking mechanism 99. A six degrees-of-freedom electromagnetic tracking system 70, e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system is utilized for performing navigation, although other configurations are also contemplated. Tracking system 70 is configured for use with catheter guide assemblies 90, 100 to track the position of the EM sensor 94 as it moves in conjunction with the EWC 96 through the airways of the patient, as detailed below.

As shown in FIG. 1, electromagnetic field generator 76 is positioned beneath the patient. Electromagnetic field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to workstation 80, which includes application 81 where sensors 74 are used to calculate a patient coordinate frame of reference.

In practice, a clinician may use the catheter guide assemblies 90, 100 to navigate the EWC 96 using the LG 92 to reach the desired surgical site or an exit location from the luminal network of the lungs (e.g. the airways). The desired surgical site may be the area within the body of the patient that is affected by a lesion. An exit location from the luminal network of the lungs may be an area within the body that is closest to a lesion such as bronchial wall nearest to the lesion. If lesions are within an area of the body where they are difficult to reach from within the luminal network of the lungs then the lesions may be reached by piercing the exit location. Once the exit location is reached, the LG 92 is removed and bronchial piercing catheter 101 is inserted into the EWC 96. Bronchial piercing catheter 101 is then advanced forward to pierce the bronchial walls while tracking its proximity to the target. Once placed in proximity to the target, the EWC 96 is also advanced forward. Bronchial piercing catheter 101 can then be removed, and a biopsy tool 102 can be inserted into the EWC 96 and advanced to the target such as the lesion to be treated. The use of the bronchial piercing catheter 101 allows the navigation of the EWC 96 to a target outside the airways.

In some embodiments, the LG 92 is integrated with the bronchial piercing catheter 101 and the bronchial piercing catheter 101 may be locked inside the EWC 96 so the distal end of the bronchial piercing catheter 101 is positioned inside the distal end of the EWC 96. Bronchial piercing catheter 101 (with the integrated LG 92) is then navigated with the EWC 96 to a desired exit location within the luminal network of the lungs. Once the exit location is reached, the bronchial piercing catheter 101 is advanced forward and locked relative to the EWC 96 in a second position in which the distal end of the bronchial piercing catheter 101 is just beyond the distal end of the EWC 96. The bronchial piercing catheter 101 and the EWC 96 are then advanced forward to pierce the bronchial walls while tracking its proximity to the target. Using a sensor integrated with a bronchial piercing catheter eliminates the step of removing the LG 92 in order to place the bronchial piercing catheter 101 through the EWC 96.

Of course, those of skill in the art will recognize that a blunt tipped dissector, or other tissue expander, including inflatable tissue expanders could be utilized in combination with the EWC 96 and the bronchial piercing catheter 101, without departing from the scope of the present disclosure. For a more detailed description of the bronchial piercing catheter 101 reference is made to commonly-owned U.S. Provisional Patent Application No. 62/279,373 filed on Jan. 15, 2016 by Herdina et al., the entire contents of each of which are hereby incorporated by reference.

If lesions are within an area of the body where they can be reached from the luminal network of the lungs then a biopsy tool, such as biopsy tool 102 may be used. Biopsy tool 102 may be inserted into the catheter guide assemblies 90, 100 following navigation to a target and removal of the LG 92. The biopsy tool 102 is used to collect one or more tissue sample from the target tissue. The biopsy tool 102 may be further configured for use in conjunction with tracking system 70 to facilitate navigation of biopsy tool 102 to the target tissue, tracking of a location of biopsy tool 102 as it is manipulated relative to the target tissue to obtain the tissue sample, and/or marking the location where the tissue sample was obtained. During navigation, EM sensor 94, in conjunction with tracking system 70, enables tracking of EM sensor 94 and/or biopsy tool 102 as EM sensor 94 or biopsy tool 102 is advanced through the patient's airways.

A variety of useable biopsy tools are described in U.S. Patent Publication Nos. 2015/0141869 and 2015/0141809 both entitled DEVICES, SYSTEMS, AND METHODS FOR NAVIGATING A BIOPSY TOOL TO A TARGET LOCATION AND OBTAINING A TISSUE SAMPLE USING THE SAME, filed Sep. 17, 2014 and U.S. Patent Publication No. 2015/0265257 having the same title and filed Dec. 9, 2014, both by Costello et al., the entire contents of each of which are incorporated herein by reference and useable with the EMN system 10 as described herein.

During procedure planning, workstation 80 utilizes computed tomographic (CT) image data for generating and viewing a three-dimensional model ("3D model") of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor 81 associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as targets to which a pathway can be planned. Once selected, the pathway is saved for use during the navigation procedure. An example of a suitable pathway planning system and method is described in U.S. Patent Publication Nos. 2014/0281961; 2014/0270441; and 2014/0282216, all entitled PATHWAY PLANNING SYSTEM AND METHOD, filed on Mar. 15, 2014, the entire contents of each of which are incorporated herein by reference.

Figure 2:
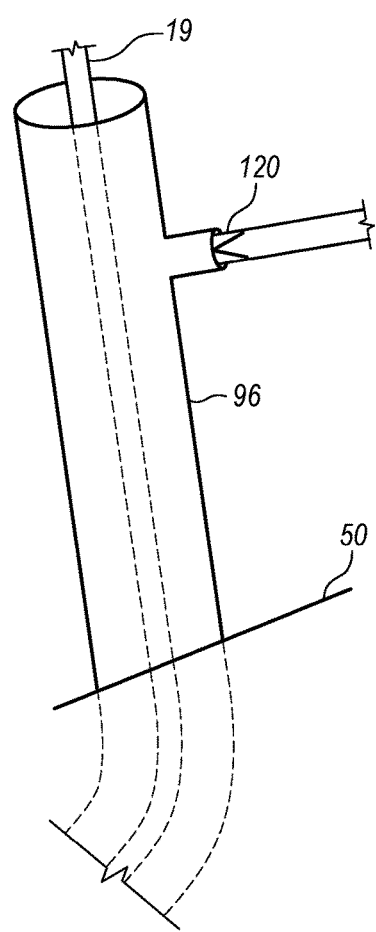
FIG. 2 is an enlarged view of a portion of an extended working channel connected to valve.

Turning now to FIG. 2, there is shown an enlarged view of a portion of EWC 96 connected to valve 120, in accordance with aspects of the present disclosure, and a portion of a medical instrument 19. Medical instrument 19 may be part of an ablation catheter, in which case medical instrument 19 is referred to herein as an ablation probe. Medical instrument 19 may be configured to be received within EWC 96. Medical instrument 19 may extend through an entire length of the EWC 96 and into bronchoscope 50. In some embodiments, medical instrument 19 may include a microwave antenna (not shown). Examples of microwave antenna construction may be found in commonly assigned U.S. Patent Pub. Nos. 2014/0276033 entitled "Microwave Energy-Device and System," and 2014/0046174 entitled "Microwave Ablation Catheter and Method of Utilizing Same," the entire contents of each is incorporated herein by reference. As depicted in FIG. 2, valve 120 may be connected to EWC 96 perpendicularly.

After navigating the EWC 96 proximate the lesion it may be desirable to secure the EWC within the airways of the patient. In accordance with one embodiment of the present disclosure, this may be done by applying a vacuum to valve 120, as will be described in greater specificity below with respect to treatment. The application of a vacuum to the EWC removes some of the air within the luminal network and can cause the luminal network to collapse onto the EWC, at least in the area proximate an opening operably connected to the valve 120. This collapsing or apposition allows for the tissue of the luminal network itself to secure the orientation of the EWC 96. This secured orientation can be verified using imaging techniques including ultrasound and fluoroscopy. Once confirmed the clinician can take the biopsy with confidence that the EWC is secured relative to the target and will acquire the desired tissue sample.

After a biopsy, in facilities utilizing Rapid Onsite Evaluation or (ROSE) the sample is analyzed for evidence of cancer or other diseases. Alternatively, following traditional evaluation techniques, if the sample is cancerous it may be desirable to treat the affected tissue. Treatment requires re-navigation of the EWC 96 to the target and insertion of a medical instrument 19 for treatment, such as a microwave ablation catheter through the EWC 96 and into the lesion or near the lesion to ablate the lesion. To ensure medical instrument 19 reaches the target tissue, bronchial piercing catheter 101 may first be inserted into a desired location in the target tissue (e.g. a tumor or mass), and then the EWC 96 may be advanced over the top of the bronchial piercing catheter 101 to secure the EWC 96 in the target tissue. The bronchial piercing catheter 101 is then removed and the medical instrument 19 can be navigated to the target tissue through the EWC 96. In some embodiments the EWC 96 may have to be retracted after placement of the microwave ablation catheter to enable operation of the ablation catheter.

Figure 3:
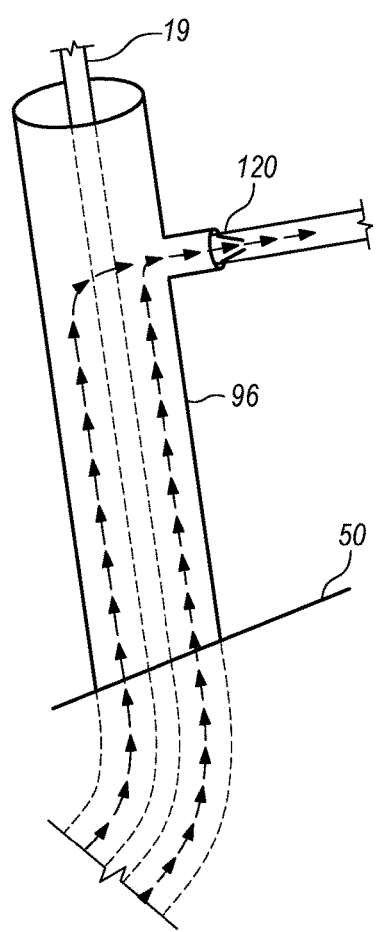
FIG. 3 illustrates flow of air through the valve connected to the extended working channel.

As described above, lesions may be partially filled with air, and puncturing a lesion or performing a biopsy of the lesion may result in the medical instrument used to the lesion to be surrounded by air. In some embodiments, a tissue-to-tool interface between energy source, medical instrument 19, and target tissue, such as tissue of the target lesion, providing a consistent environment for energy delivery may be created suctioning air surrounding the energy source, medical instrument 19. The air may be suctioned out of the luminal network by application of suction to valve 120. FIG. 3 illustrates the flow of air 301 away from distal end of EWC 96 and through valve 120. As described above, a vacuum source (not shown) may be connected to valve 120 to suction some or all of the air surrounding the EWC 96 or medical instrument 19. The vacuum source may include, but not limited to, a syringe or a pump.

Figure 4:
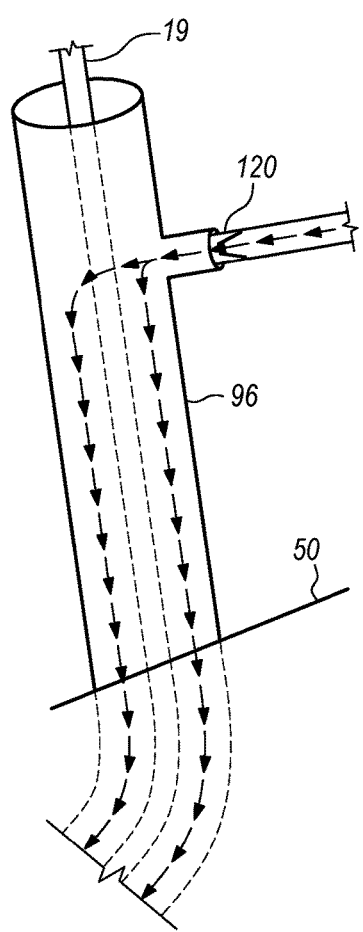
FIG. 4 illustrates flow of fluid through the valve connected to the extended working channel.

In some embodiments, a tissue-to-tool interface between medical instrument 19 and target tissue may be created by injecting a fluid into valve 120. The injected fluid may provide a more consistent environment for energy delivery by a medical instrument 19 such as a microwave ablation catheter. The flow of fluid injected into valve 120 is depicted in FIG. 4 as flow 401. The fluid injected into valve 120 may be any conductive fluid including, but not limited to, saline. In some embodiments, valve 120 may be a one-way valve. One-way valve 120 may include a duckbill seal. The duckbill seal may be configured with two states, a biased state and an unbiased state. In the biased state, fluid is allowed to pass through the duckbill, valve 120, towards the distal end of medical instrument 19. The biased state may also be referred to herein as when the duckbill is in an open state. In the unbiased state, no fluid passes through the duckbill or valve 120.

The tissue-to-tool interface described in combination with isolation of the medical instrument 19 and the target tissue from other areas of the luminal network increases efficiency in delivery of energy, such as microwave energy. In embodiments employing suction, the tissue-to-tool interface created by the apposition of the tool and the target tissue improves delivery of therapeutic substances to the target tissue, and can eliminate or reduce leakage of therapeutic substance away from the target area. Additionally, the apposition of the tool with the target tissue allows for improved delivery of energy (e.g., microwave energy) and sonic waves (e.g., ultrasound waves) by eliminating nonconductive interfaces between the tool and the target tissue. Similarly, isolation and injection of a fluid into the luminal network homogenizes the environment through which energy (e.g., microwave or ultrasound) must travel and improves the transfer of energy for better treatment and imaging.

As depicted in FIG. 3 and FIG. 4, air flow 301 and fluid flow 401 flows while medical instrument 19 is positioned within EWC 96. As a result, air flow 301 and fluid flow 401 flows in a space defined between medical instrument 19 and EWC 96. Additional details of a flow in a space provided between an energy source and an EWC is provided herein in FIG. 5.

Figure 5:
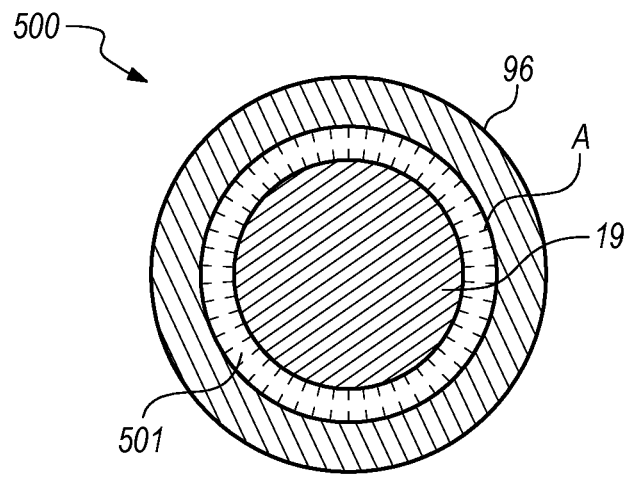
FIG. 5 is a cross-sectional view of a portion of extended working channel.

Turning now to FIG. 5, there is shown a cross-sectional view of EWC 96 that illustrates a space between medical instrument 19 and EWC 96. The cross-sectional view 500 illustrates the EWC 96 and medical instrument 19 positioned within the EWC 96. Space 501 is annularly defined between the EWC 96 and the medical instrument 19. Flow A, which may be air flow 301 or fluid flow 401 flows within space 501. Flow A travels along the length of bronchoscope 50, via the EWC 96. Flow A does not directly contact the bronchoscope 50, but stays within EWC 96 until it exits EWC 96. Flow A flows circumferentially around the ablation medical instrument 19 within the annular space 119. In this way, EWC 96 (or primary channel) achieves the dual purpose of allowing a clinician to simultaneously use/manipulate a surgical instrument and create a tool-to-tissue interface between instrument and tissue through EWC 96. Though shown here as ending at the distal end of the EWC 96 the annular space 119 may also terminate in one or more openings formed on the side of the EWC 96. As such, the apposition of tissue to the EWC 96 and medical instrument 19 may be enhanced and promote greater sealing characteristics.

Figure 6:
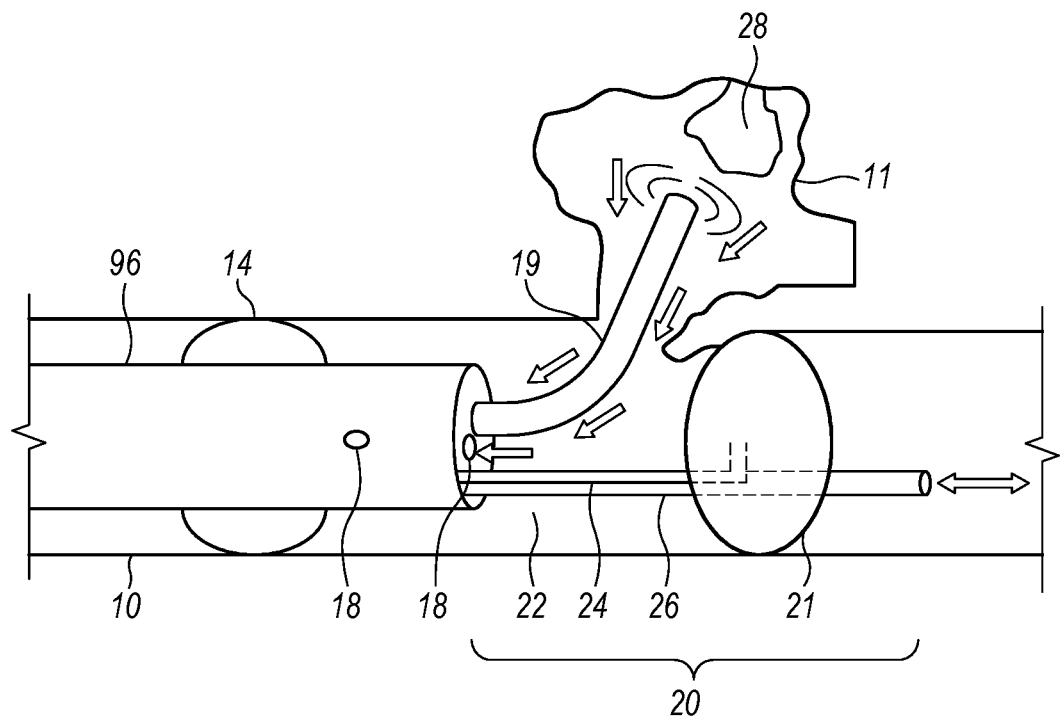
FIG. 6 is an enlarged view of a portion of an extended working channel comprising a port or opening and balloons within an airway of a patient.

Turning now to FIG. 6 there is shown an enlarged view of a portion of an extended working channel 96 comprising a port or opening 18 and balloons 14, 21 within an airway of a patient. FIG. 6 depicts an airway 10, an alveolus 11 that branches off airway 10, and a lesion 28 that is formed within alveolus 11. EWC 96 is inserted into airway 10 and a proximal balloon 14 extends from EWC 96. Balloon 14 may extend laterally from EWC 96, as depicted in FIG. 6, and seal the portion of the airway 10 proximal of the distal end of EWC 96. Medical instrument 19 extends from the distal end of EWC 96. Medical instrument 19, as described above, may be a microwave ablation catheter. In some embodiments, medical instrument 19 may be a catheter configured to deliver therapeutic substance, such as a chemotherapy substance, to the target tissue.

In at least one embodiment a balloon catheter 20 extends from EWC 96 and includes balloon 21 at the distal end of catheter 20. Fluid line 22 is in fluid communication with balloon 21. In some embodiments, fluid line 22 may be a dual fluid line that includes a first fluid line 24 and a second fluid line 26. In some embodiments, balloon 21 may be expanded by application of fluid through fluid line 22. Fluid may be applied to the balloon 21 through a fluid line attached to the balloon, such as fluid line 24. Fluid line 22 passes through distal balloon 21 and fluidly connects a portion of airway 10 with atmosphere or a ventilation device (not shown) that permits lung comprising airway 10 to receive and expel air. Balloons 14 and 21 create an area in airway 10 that is effectively sealed from the atmosphere.

Port 18 located on the distal portion of EWC 96 and is in fluid communication through EWC 96 to a vacuum source, such as a pump or syringe (not shown). A tissue-to-tool interface between medical instrument 19 and lesion 28, providing a consistent environment or zone may be created by suctioning air surrounding the medical instrument 19. The vacuum generated by vacuum source is sufficient to place medical instrument 19 in apposition with tissue of lesion 28, but not necessarily enough to cause atelectasis or collapse of alveolus 11.

In embodiments where medical instrument 19 is an energy delivery probe, such as a microwave ablation probe, the tissue-to-tool interface created between medical instrument 19 and lesion 28 improves delivery of energy to the lesion 28 because the non-conductive interface, (i.e., the air between medical instrument 19 and lesion 28), is substantially eliminated. In embodiments where medical instrument 19 delivers a therapeutic substance the tissue-to-tool interface created between medical instrument 19 and lesion 28 improves delivery of the therapeutic substance to lesion 28 by eliminating leakage of the therapeutic substance beyond the portion of the airway 10 isolated by balloons 14 and 21, thus limiting the therapeutic substance to those areas where they will be most effective, namely alveolus 11 and a small section of airway 10.

Figure 7A:
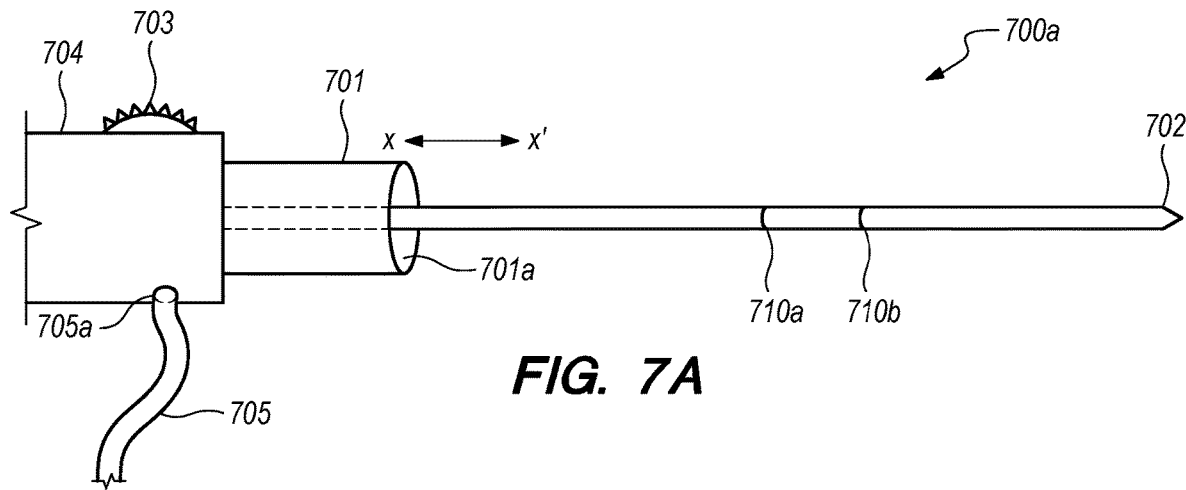
FIG. 7a is an enlarged view of a medical instrument configured for percutaneously accessing and treating a target tissue.

Turning now to FIG. 7a, there is shown an enlarged view of a medical instrument 700a for percutaneously accessing and treating a target tissue. Medical instrument 700a includes a handle 704 coupled with an ablation probe 702. In some embodiments, ablation probe 702 extends from handle 704. Ablation probe 702 includes a microwave ablation antenna (not shown) that is used to ablate tissue. Handle 704 includes a housing unit (not shown) configured to house catheter 701. Catheter 701 is optionally configured to extend out from the housing unit within handle 704 and retract into the housing unit within handle 704. Catheter 701 defines a lumen 701a and ablation probe 702 is located within lumen 701a.

A control unit, such as wheel 703, is configured to control the extension and retraction of catheter 701 such that rotating wheel 703 away from the clinician holding handle 704 or in the direction X' extends catheter 701 by moving catheter 701 in the direction X' and rotating wheel 703 towards the clinician holding handle 704 or in the direction X retracts catheter 701 into the housing unit of handle 704 by moving catheter 701 in the direction X. In some embodiments, the control unit may be a slider, where sliding the slider away from the clinician holding handle 704 or in the direction X' extends the catheter 701 and sliding the slider towards the clinician holding handle 704 or in the direction X retracts the catheter 701. Alternatively the catheter 701 may be formed of a trocar or other component inserted into the patient proximate the target tissue through which the ablation probe 702 is inserted in accordance with embodiments of the present disclosure.

Medical instrument 700a may include one or more markers, such as markers 710a, 710b, to help guide a clinician in determining how far to extend the catheter in order to most efficiently create the tissue-to-tool interface, described herein, between the ablation probe 702 and a target tissue, such as a lesion. Each of the markers indicates a different length of extension and based on how deep ablation probe 702 is inserted into a patient, a marker may more effectively create the desired tissue-to-tool interface than other markers.

Catheter 701, via port 705a and tube 705, is in fluid communication with a vacuum source (not shown) or a liquid source (not shown). Port 705a is in fluid communication with lumen 701a of the catheter 701. Tube 705 is configured and coupled with catheter 701, via port 705a, such that one end of tube 705 is attached to an end of lumen 701a of catheter 701 that is proximal to the clinician, via port 705a, and the other end of tube 705 is coupled with the vacuum or liquid source. As described above, the vacuum source described herein includes, but is not limited to, a pump or a syringe. The vacuum source generates a vacuum by suctioning air, through tube 705, via lumen 701a, around ablation probe 702. The application of vacuum is sufficient to place ablation probe 702 in apposition with the target tissue, thus, creating a consistent zone around ablation probe 702, but not enough to cause atelectasis. Also as described above, a liquid source, as described herein, provides a fluid such as saline. The fluid from the liquid source helps create a consistent zone around ablation probe 702 by injecting fluid from the liquid source through tube 705 and onto at least a portion of the target tissue, via lumen 701a.

Figure 7B:
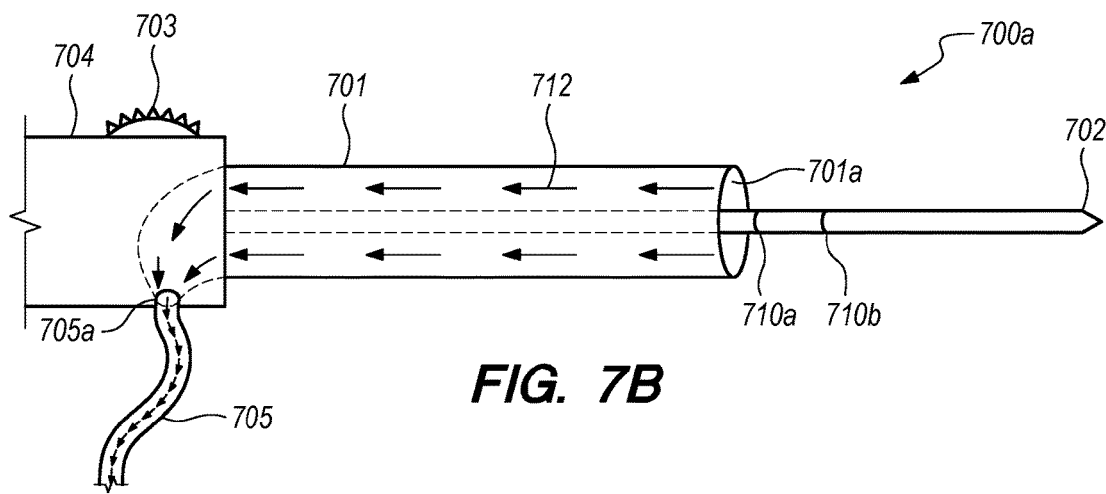
FIG. 7b illustrates flow of air through a catheter housed within the medical instrument configured for percutaneously accessing and treating a target tissue.
Figure 7C:
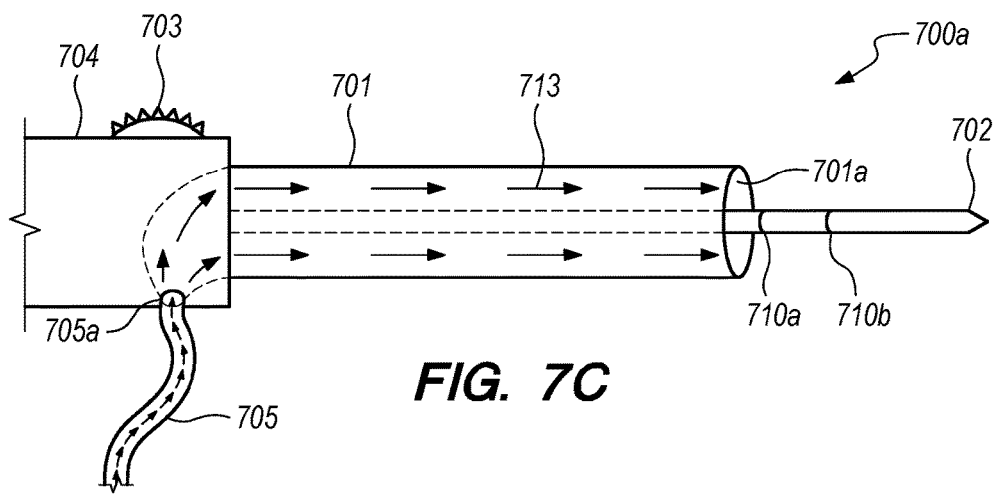
FIG. 7c illustrates flow of fluid through the catheter housed within the medical instrument configured for percutaneously accessing and treating a target tissue.

Turning now to FIG. 7b, there is shown a medical instrument 700a with the catheter 701 extended to marker 710a and in a fluid communication with a vacuum source (not shown). As depicted by airflow 712, air is suctioned away from target tissue through lumen 701a, which is in fluid communication with tube 705, via port 705a. As described above, suctioning sufficient amount of air away from target tissue places the target tissue in apposition with the target tissue, which creates a more consistent zone around ablation probe 702. FIG. 7c illustrates medical instrument 700a with the catheter 701 in a fluid communication with a liquid source, which provides a fluid, such as saline. Fluid flow 713 depicts the flow of fluid, for example saline, onto the target tissue, through lumen 701a, which is in fluid communication with tube 705, via port 705a, in order to form a consistent zone around ablation probe 702. Thus, a tissue-to-tool interface is created while accessing and treating target tissue percutaneously.

Figure 7D:
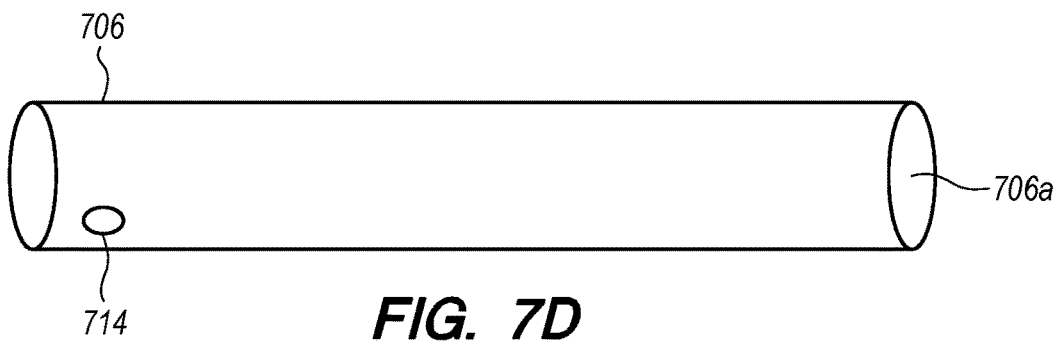
FIG. 7d is an enlarged view of a catheter with an opening on its side.

Turning now to FIG. 7d, there is shown an embodiment of a catheter that may be attached to the medical instrument 700a instead of being housed in medical instrument 700a. Catheter 706 defines a lumen 706a and includes a port 714, which is configured to be in fluid communication with a vacuum source or a liquid source. Port 714 is in fluid communication with lumen 706a of catheter 706. While a single catheter 706 is depicted in FIG. 7d, a plurality of catheters 706, each of a different length may be used and selection of a particular catheter 706 may be based on how deep ablation probe 702 is inserted into a patient. Catheter 706 may be attached to the medical instrument 700a by fastening it into medical instrument 700a using opening 707 on the handle 704, as depicted in FIG. 7e.

Figure 7E:
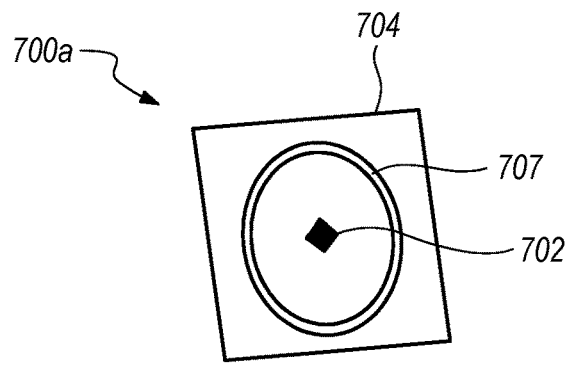
FIG. 7e is an enlarged cross-sectional view of the medical instrument configured for percutaneously accessing and treating a target tissue with an opening on its handle portion.
Figure 7F:
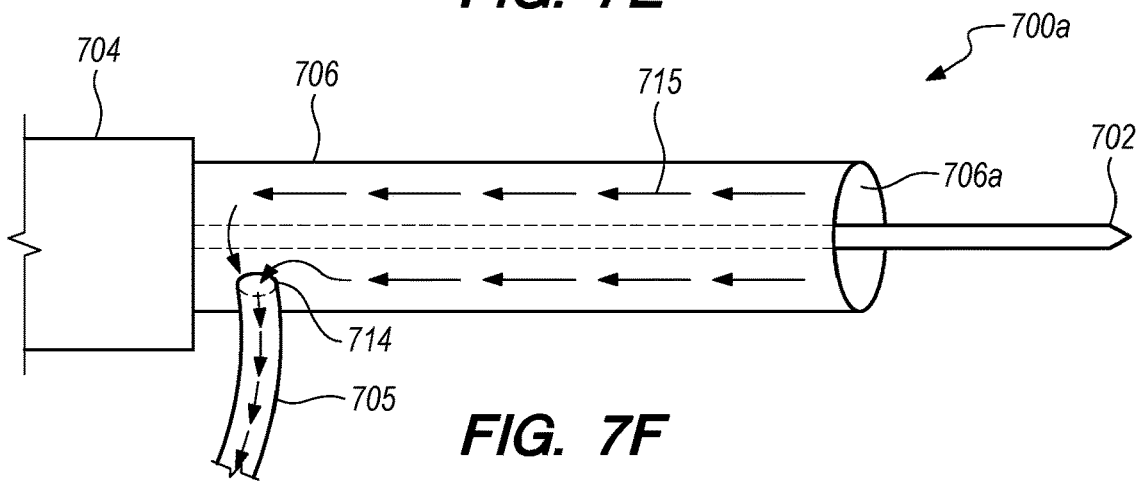
FIG. 7f is an enlarged view of a catheter fastened into the medical instrument configured for percutaneously accessing and treating a target tissue and flow of air through the catheter.
Figure 7G:
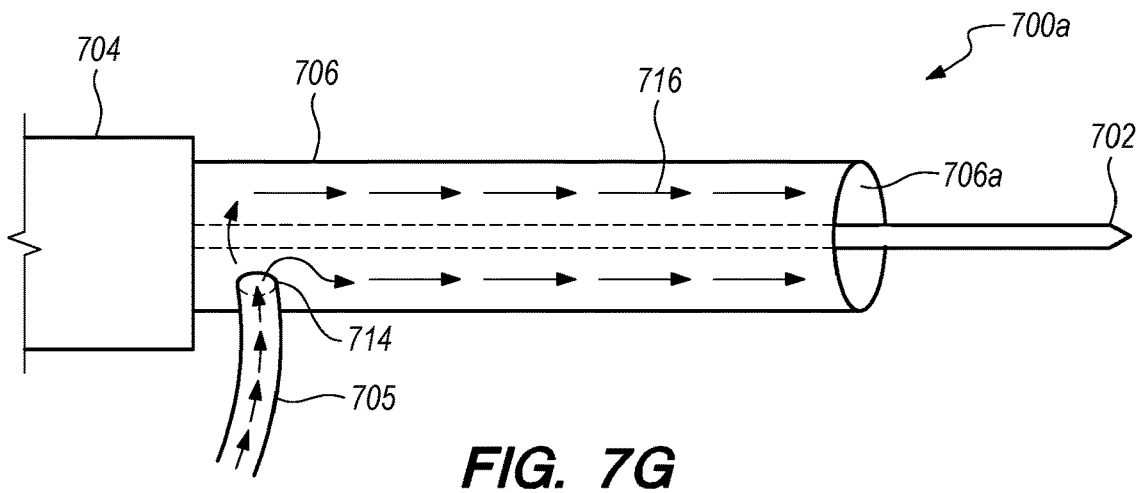
FIG. 7g is an enlarged view of a catheter fastened into the medical instrument configured for percutaneously accessing and treating a target tissue and flow of fluid through the catheter.

Turning now to FIG. 7e, there is shown a cross-sectional view of medical instrument 700a without attachment of catheter 706 to medical instrument 700a. The end of catheter 706 that is proximal to port 714 may be configured with an external thread profile (not shown) to allow catheter 706 to be fastened into opening 707 on the handle 704. Opening 707 may be configured with an internal thread profile (not shown) to accept catheter 706. Catheter 706 may be attached to the medical instrument 700a by fastening it into medical instrument 700a using opening 707. Other connection mechanisms including press fittings, suction fittings, and the like are within the scope of the present disclosure. Once fastened into opening 707, catheter 706 surrounds ablation probe 702 as illustrated in FIGS. 7f-7g. FIG. 7f illustrates port 714 being in fluid communication with a vacuum source (not shown) via tube 705. The tissue-to-tool interface, described above, is created by suctioning air away from target tissue through lumen 706a, using the vacuum source in fluid communication with port 714 via tube 705, as depicted by air flow 715. Thus, placing ablation probe 702 in apposition with target tissue and forming a consistent zone around the ablation probe. FIG. 7g illustrates port 714 being in fluid communication with a liquid source, which provides fluid, such as saline. The fluid may be injected onto at least a portion of target tissue using tube 705 and lumen 706a of catheter 706, as depicted by liquid flow 716. Thus, forming a consistent zone around ablation probe 702.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure Like reference numerals may refer to similar or identical elements throughout the description of the figures.

The phrases "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A system for use with a bronchoscope, comprising:
an extended working channel defining an elongated passageway and configured to be inserted through a bronchoscope and into a luminal network;
a valve extending through a lumen formed by a proximal end portion of the extended working channel, the lumen extending at an angle to a longitudinal axis defined by the extended working channel, the valve during use being located outside the bronchoscope and in fluid communication with the luminal network; and
a medical instrument configured for insertion through the extended working channel and into the luminal network;
wherein during operation, a vacuum source applies suction to the valve to remove air from the luminal network via the lumen, the applied suction causing tissue of the luminal network to move toward the extended working channel or the medical instrument such that the tissue of the luminal network forms a seal around an outer surface of the extended working channel or the medical instrument, thereby isolating at least a portion of the luminal network in which the extended working channel is inserted and securing an orientation of the extended working channel relative to a target within the luminal network.

2. The system of claim 1, wherein the vacuum source is a syringe.

3. The system of claim 1, wherein the vacuum source generates a threshold amount of suction to remove air from at least a portion of a luminal network in which the extended working channel is inserted.

4. The system of claim 3, wherein during the operation, a consistent zone around the medical instrument is created by suctioning the air from at least a portion of a luminal network in which the extended working channel is inserted using a distal opening of the extended working channel.

5. The system of claim 3, wherein the liquid source comprises saline.

6. The system of claim 1, wherein the lumen is in fluid communication with a liquid source.

7. The system of claim 6, wherein the valve is in fluid communication with the liquid source and a distal opening of the extended working channel.

8. The system of claim 6, wherein during operation, a consistent zone around the medical instrument is created by injecting fluid from the fluid source through the valve and into at least a portion of a luminal network in which the extended working channel is inserted.

9. The system of claim 1, wherein the valve comprises a duckbill.

10. The system of claim 1, further comprising one or more balloons operably associated with the extended working channel to secure the extended working channel within the luminal network and isolate at least a portion of the luminal network.

11. The system of claim 1, wherein the extended working channel defines a distal opening located proximal of a distal end of the extended working channel and in fluid communication with the luminal network and the valve, the distal opening in use being located outside the bronchoscope and within the luminal network.

12. A system for use with a bronchoscope, comprising:
an extended working channel configured to be inserted through a bronchoscope and into a luminal network of a patient;
a lumen formed by a proximal end portion of the extended working channel and extending at an angle to a longitudinal axis defined by the extended working channel, the lumen in fluid communication with the luminal network;
a valve extending through the lumen, the valve during use being located outside the bronchoscope and being in fluid communication with the luminal network; and
a vacuum source configured to be fluidly coupled to the valve to remove air from the luminal network via the lumen, the removal of air from the luminal network collapsing the luminal network onto the extended working channel such that tissue of the luminal network forms a seal around an outer surface of the extended working channel to secure an orientation of the extended working channel relative to a target within the luminal network.

13. The system of claim 12, wherein the lumen extends perpendicularly from the proximal end portion of the extended working channel.

14. The system of claim 12, further comprising a medical instrument configured to be inserted through the extended working channel such that the medical instrument extends from a distal end of the extended working channel into the luminal network and in proximity to the target.

15. The system of claim 14, wherein removal of air from the luminal network via the lumen collapses the luminal network onto the medical instrument to isolate the target and the medical instrument within a portion of the luminal network in which the medical instrument is inserted.

16. The system of claim 14, further comprising a liquid source configured to be fluidly coupled to the valve to inject liquid into the luminal network via the lumen, the injected liquid facilitating transfer of energy from the medical instrument to the target.

17. A system for use with a bronchoscope, comprising:
an extended working channel configured to be inserted through a bronchoscope and into a luminal network of a patient;
a medical instrument configured to be inserted through the extended working channel such that the medical instrument extends from a distal end of the extended working channel into the luminal network and in proximity to a target within the luminal network;
a first opening defined by a distal portion of the extended working channel and in fluid communication with the luminal network, the first opening during use being located outside the bronchoscope and within the luminal network;
a lumen formed by a proximal end portion of the extended working channel, the lumen extending at an angle to a longitudinal axis defined by the extended working channel, the lumen defining a second opening in fluid communication with the luminal network via the first opening;
a valve extending through the lumen, the valve during use being located outside the bronchoscope and in fluid communication with the luminal network via the first opening; and
a vacuum source configured to be fluidly coupled to the valve to remove air from the luminal network such that tissue of the luminal network forms a seal around an outer surface of the extended working channel.

18. The system of claim 17, wherein the seal formed around the outer surface of the extended working channel secures an orientation of the extended working channel relative to the target.

19. The system of claim 17, wherein removal of air from the luminal network collapses the luminal network onto the medical instrument to isolate the target and the medical instrument within a portion of the luminal network in which the medical instrument is inserted.

\* \* \* \* \*